US011071704B2

(12) United States Patent
Sato

(10) Patent No.: US 11,071,704 B2
(45) Date of Patent: Jul. 27, 2021

(54) ORAL COMPOSITION

(71) Applicant: Kao Corporation, Tokyo (JP)

(72) Inventor: Tomoya Sato, Tokyo (JP)

(73) Assignee: Kao Corporation, Tokyo (JP)

(*) Notice: Subject to any disclaimer, the term of this patent is extended or adjusted under 35 U.S.C. 154(b) by 0 days.

(21) Appl. No.: 16/770,788

(22) PCT Filed: Nov. 14, 2018

(86) PCT No.: PCT/JP2018/042120
§ 371 (c)(1),
(2) Date: Jun. 8, 2020

(87) PCT Pub. No.: WO2019/130871
PCT Pub. Date: Jul. 4, 2019

(65) Prior Publication Data
US 2021/0177720 A1 Jun. 17, 2021

(30) Foreign Application Priority Data
Dec. 27, 2017 (JP) .............................. JP2017-251506

(51) Int. Cl.
A61K 8/46 (2006.01)
A61K 8/34 (2006.01)
A61Q 11/00 (2006.01)
A61K 8/19 (2006.01)
A61K 8/365 (2006.01)

(52) U.S. Cl.
CPC ............... A61K 8/466 (2013.01); A61K 8/19 (2013.01); A61K 8/347 (2013.01); A61K 8/365 (2013.01); A61Q 11/00 (2013.01)

(58) Field of Classification Search
CPC . A61K 8/19; A61K 8/24; A61K 8/466; A61K 8/00
USPC .......................................................... 424/56
See application file for complete search history.

(56) References Cited

U.S. PATENT DOCUMENTS

| 3,409,637 | A | | 11/1968 | Eccles et al. |
| 3,420,875 | A | | 1/1969 | Di Salvo et al. |
| 3,462,525 | A | * | 8/1969 | Levinsky ............... A61K 8/466 424/56 |
| 5,078,916 | A | | 1/1992 | Kok et al. |
| 6,656,454 | B1 | | 12/2003 | Koester et al. |
| 2014/0080746 | A1 | | 3/2014 | Doi et al. |
| 2019/0175474 | A1 | | 6/2019 | Sato |

FOREIGN PATENT DOCUMENTS

| IN | 3692/CHE/2012 | * | 7/2014 | ............... A61K 8/00 |
| JP | S50-000898 B1 | | 1/1975 | |
| JP | 2003-524678 A | | 8/2003 | |
| JP | 2006-347986 A | | 12/2006 | |
| JP | 2008-074772 A | | 4/2008 | |
| JP | 2011-132169 A | | 7/2011 | |
| JP | 2011-195552 | | 10/2011 | |
| JP | 2013-151474 A | | 8/2013 | |
| JP | 2015-020970 A | | 2/2015 | |
| JP | 2015-27974 A | | 2/2015 | |
| JP | 5910354 B2 | | 4/2016 | |
| JP | 2018-039786 A | | 3/2018 | |

OTHER PUBLICATIONS

International Search Report for PCT/JP2018/042120; I.A. fd Nov. 14, 2018, dated Feb. 19, 2019, from the Japan Patent Office, Tokyo, Japan.
International Preliminary Report on Patentability (IPRP), Chapter I of the Patent Cooperation Treaty, including the Written Opinion, for PCT/JP2018/042120; I.A. fd Nov. 14, 2018, dated Jun. 30, 2020, by the International Bureau of WIPO, Geneva, Switzerland.

* cited by examiner

Primary Examiner — Walter E Webb
(74) Attorney, Agent, or Firm — Sterne, Kessler, Goldstein & Fox P.L.L.C.

(57) ABSTRACT

The present invention relates to an oral composition which contains an oil soluble active component such as isopropyl methylphenol and triclosan and an anionic surfactant in combination and is capable of enhancing adsorption of the oil soluble active component on the tooth surface to demonstrate an excellent biofilm formation inhibitory effect.
The oral composition comprises the following components (A), (B), (C), and (D):
(A) an olefin sulfonic acid having 14 or more and 20 or less carbon atoms or a salt thereof,
(B) a hydroxyalkanesulfonic acid having 14 or more and 20 or less carbon atoms or a salt thereof,
(C) one or more oil soluble active components selected from the group consisting of isopropyl methylphenol, triclosan, thymol, and β-glycyrrhetinic acid, and
(D) a water-soluble alkali metal salt,
wherein the total content of the component (A) and the component (B) is 0.001 mass % or more and 2.5 mass % or less, and the content of the component (A) is 3 mass % or more and 50 mass % or less in the total content of the component (A) and the component (B).

18 Claims, No Drawings

ORAL COMPOSITION

FIELD OF THE INVENTION

The present invention relates to an oral composition.

BACKGROUND OF THE INVENTION

Dental plaque (plaque) is a mass which is formed by exopolysaccharides (EPS) produced by bacteria present in the oral cavity and in which bacteria grow internally and deeply, is known as one type of the so-called biofilms, and firmly attaches to the tooth surface. Such a dental plaque causes stickiness in the oral cavity and halitosis, which may cause not only discomfort but also dental caries, tartar, periodontal diseases and the like. For this reason, various agents and compositions applicable to the oral cavity have been developed by using various surfactants having a cleansing action to remove such a dental plaque and biofilm.

For example, Patent Literature 1 discloses an oral biofilm removing-agent containing an anionic surfactant such as an α-olefin sulfonate, dextranase, and a sugar alcohol in combination, which enhances an effect to disperse and remove oral biofilm. Further, Patent Literature 2 discloses an oral composition containing an α-olefin sulfonate having 14 carbon atoms and an acyl amino acid salt and/or arginine, which attempts to enhance an effect of removing oral biofilms while inhibiting the bitterness peculiar to anionic surfactants. Such an α-olefin sulfonate, as described in Patent Literature 1, is known to possibly contain about 20 mass % or less of a hydroxyalkyl sulfonate as a by-product.

On the other hand, isopropyl methylphenol, triclosan and the like are known as an oil soluble component applicable to an oral composition and have been frequently used to achieve desired effects. For example, Patent Literature 3 discloses a liquid oral composition which contains cetylpyridinium chloride, a calcium salt and a nonionic surfactant in combination with such an oil soluble component, which attempts to enhance an effect of adsorbing cetylpyridinium chloride on the tooth surface.
(Patent Literature 1) JP-A-2015-20970
(Patent Literature 2) JP-A-2013-151474
(Patent Literature 3) JP-A-2011-132169

SUMMARY OF THE INVENTION

The present invention provides an oral composition comprising the following components (A), (B), (C), and (D):

(A) an olefin sulfonic acid having 14 or more and 20 or less carbon atoms or a salt thereof, (B) a hydroxyalkanesulfonic acid having 14 or more and 20 or less carbon atoms or a salt thereof, (C) one or more oil soluble active components selected from the group consisting of isopropyl methylphenol, triclosan, thymol, and β-glycyrrhetinic acid, and (D) a water-soluble alkali metal salt, wherein the total content of the component (A) and the component (B) is 0.001 mass % or more and 2.5 mass % or less, and the content of the component (A) is 3 mass % or more and 50 mass % or less in the total content of the component (A) and the component (B).

When attempting to demonstrate a biofilm formation inhibitory effect by, as described in the above Patent Literature 3, allowing oil soluble components such as isopropyl methylphenol and triclosan to act as an active component instead of cetylpyridinium chloride, the adsorption of such components on the tooth surface is still unsatisfactory by the technology described in such Patent Literature. Even inclusion of an anionic surfactant such as an α-olefin sulfonate described in Patent Literatures 1 and 2 in combination fails to fully enhance the delivery of these oil soluble components to the tooth surface, leaving the circumstances requiring further improvement.

Namely, the present invention relates to an oral composition which contains an oil soluble active component such as isopropyl methylphenol and triclosan and an anionic surfactant in combination and is capable of enhancing the adsorption of the oil soluble active component on the tooth surface to demonstrate an excellent biofilm formation inhibitory effect.

Thus, the present inventor conducted extensive studies and found that when the content of an olefin sulfonic acid or a salt thereof as an anionic surfactant is controlled and a hydroxyalkyl sulfonic acid or a salt thereof which has been acknowledged only as a by-product is allowed to be present in a large amount while these are contained in combination with an oil soluble active component such as isopropyl methylphenol and triclosan and a water-soluble alkali metal salt, the delivery of the oil soluble active component to the tooth surface is enhanced and excellent adsorption of these components on the tooth surface is demonstrated, thereby to improve a biofilm formation inhibitory effect.

According to the oral composition of the present invention, an oil soluble active component such as isopropyl methylphenol and triclosan is effectively and efficiently delivered to the tooth surface, the adsorption on the tooth surface is notably enhanced, an excellent biofilm formation inhibitory effect can be demonstrated, and further good foaming and excellent composition stability can be imparted.

DETAILED DESCRIPTION OF THE INVENTION

Hereinafter, the present invention is described in detail.

The oral composition of the present invention comprises the following components (A), (B), (C), and (D):

(A) an olefin sulfonic acid having 14 or more and 20 or less carbon atoms or a salt thereof, (B) a hydroxyalkanesulfonic acid having 14 or more and 20 or less carbon atoms or a salt thereof, (C) one or more oil soluble active components selected from the group consisting of isopropyl methylphenol, triclosan, thymol, and β-glycyrrhetinic acid, and (D) a water-soluble alkali metal salt, wherein the total content of the component (A) and the component (B) is 0.001 mass % or more and 2.5 mass % or less, and the content of the component (A) is 3 mass % or more and 5 mass % or less in the total content of the component (A) and the component (B).

The oral composition of the present invention contains, as the component (A), an olefin sulfonic acid having 14 or more and 20 or less carbon atoms or a salt thereof. Such an olefin sulfonic acid or a salt thereof can be obtained by using an olefin having a double bond along the main chain as a raw material, sulfonating the olefin, neutralizing and hydrolyzing, followed by purifying such an olefin. On the other hand, a hydroxyalkanesulfonic acid or a salt thereof, which is the component (B) to be described later, is a hydroxy compound of the component (A) and produced when the component (A) is obtained.

The olefin sulfonic acid or a salt thereof of the component (A) has 14 or more, and preferably 16 or more carbon atoms from a viewpoint of effectively enhancing the adsorption of the component (C) on the tooth surface. The olefin sulfonic acid or a salt thereof of the component (A) has 20 or less, and preferably 18 or less carbon atoms from a viewpoint of favorably maintaining the delivery of the component (C) to the tooth surface and the composition stability. Of them, the olefin sulfonic acid or a salt thereof of the component (A) has more preferably 18 carbon atoms from a viewpoint of furthermore effectively enhancing the adsorption of the component (C) on the tooth surface and more preferably 16 carbon atoms from a viewpoint of imparting favorable foaming and foam densifying property when used.

Note that such a number of carbon atoms is derived from an olefin used as a raw material, and an olefin sulfonic acid having the number of carbon atoms other than the above or a salt thereof may also be contained depending on a raw material to be used.

The oral composition of the present invention contains, as the component (B), a hydroxyalkanesulfonic acid having 14 or more and 20 or less carbon atoms or a salt thereof. The hydroxyalkanesulfonic acid or a salt thereof of the component (B) has 14 or more, and preferably 16 or more carbon atoms from a viewpoint of effectively enhancing the adsorption of the component (C) on the tooth surface. The hydroxyalkanesulfonic acid or a salt thereof of the component (B) has 20 or less, and preferably 18 or less carbon atoms from a viewpoint of favorably maintaining the delivery of the component (C) to the tooth surface and the composition stability. Of them, the hydroxyalkanesulfonic acid or a salt thereof of the component (B) has more preferably 18 carbon atoms from a viewpoint of furthermore enhancing the adsorption of the component (C) on the tooth surface, and more preferably 16 carbon atoms from a viewpoint of imparting favorable foaming and foam densifying property when used.

Note that such a number of carbon atoms is derived from an olefin used as a raw material (raw material olefin), and a raw material olefin different from the raw material olefin of the component (A) may be used, namely, the component (A) may have the number of carbon atoms different from that of the component (B).

More specifically, for example, the total content of an olefin sulfonic acid having 18 carbon atoms or a salt thereof (a-2) and a hydroxyalkanesulfonic acid having 18 carbon atom or a salt thereof (b-2) is preferably from 50 to 100 mass %, more preferably from 70 to 100 mass %, further preferably from 90 to 100 mass %, and furthermore preferably from 95 to 100 mass % in the total content of the component (A) and the component (B) from a viewpoint of furthermore effectively enhancing the adsorption of the component (C) on tooth surfaces. Further, the total content of an olefin sulfonic acid having 16 carbon atoms or a salt thereof (a-1) and a hydroxyalkanesulfonic acid having 16 carbon atoms or a salt thereof (b-1) is preferably from 90 to 100 mass %, and furthermore preferably from 95 to 100 mass % in the total content of the component (A) and the component (B) from a viewpoint of comfortable foaming of the composition.

Note that the content of the component (A) and the content of the component (B) mean values in terms of acid, and the same applies to the total content of these and the component (a-1), the component (a-2), the component (b-1), and the component (b-2). Namely, for example, the content of the component (A) represents a value in terms of an olefin sulfonic acid, and the content of the component (B) represents a value in terms of an alkanesulfonic acid.

In the oral composition of the present invention, the content of the above component (A) is 3 mass % or more and 50 mass % or less in the total content of the component (A) and the component (B). Paying attention that the component (B), which has been conventionally acknowledged only as a by-product and has been limited in the content, is a useful component to effectively enhance the adsorption of the component (C) on the tooth surface and further enhances, together with the component (D), the delivery to the tooth surface of the component (C) contributing to the development of excellent adsorption, the present inventor sets the content of the component (A) as above and increases the content of the hydroxy compound, which is the component (B), preferably more than the content of the olefin compound, which is the component (A), to thereby notably enhance the biofilm formation inhibitory effect.

From a viewpoint of effectively enhancing the adsorption of the component (C) on tooth surfaces, the content of the component (A) is specifically 50 mass % or less, preferably 45 mass % or less, more preferably 30 mass % or less, further preferably 25 mass % or less, and furthermore preferably 20 mass % or less, in the total content of the component (A) and the component (B). Further, from a viewpoint of favorably maintaining the delivery capacity of the component (C) to tooth surfaces and the composition stability, the content of the component (A) is 3 mass % or more, preferably 5 mass % or more, more preferably 7 mass % or more, further preferably 9 mass % or more, and furthermore preferably 10 mass % or more, in the total content of the component (A) and the component (B). Additionally, the content of the component (A) is 3 mass % or more and 50 mass % or less, preferably from 5 to 50 mass %, more preferably from 7 to 45 mass %, further preferably from 9 to 30 mass %, further preferably from 9 to 25 mass %, and further preferably from 10 to 20 mass % in the total content of the component (A) and the component (B).

Note that the content of the component (A) in the total content of the component (A) and the component (B) can be measured using High Performance Liquid Chromatography-Mass Spectrometer (HPLC-MS). Specifically, the hydroxy compound and the olefin compound are separated from the active components by HPLC and subjected to an MS to identify the component (A), and the content of the component (A) in the total content of the component (A) and the component (B) can be determined from the HPLC-MS peak area. More specifically, the content of the component (A) can be measured using an HPLC system "Agilent Technology 1100" (manufactured by Agilent Technologies, Inc.), column "L-column ODS 4.6×150 mm" (manufactured by Chemical Evaluation and Research Institute, Japan) under the following conditions.

Sample preparation (diluted 1,000-fold with methanol), eluent A (10 mM ammonium acetate added water), eluent B (10 mM ammonium acetate added methanol), gradients (0 min.(A/B=30/70%)→10 min. (30/70%)→55 min. (0/100%) →65 min. (0/100%)→66 min. (30/70%)→75 min. (30/70%)), MS system "Agilent Technology 1100 MS SL (G1946D))" (manufactured by Agilent Technologies, Inc.), MS detection (anion detection m/z60-1600, UV 240 nm).

Further, from a viewpoint of further enhancing low temperature storage stability of the composition, the mass ratio of the total content of an olefin sulfonic acid having 16 carbon atoms or a salt thereof (a-1) and a hydroxyalkanesulfonic acid having 16 carbon atoms or a salt thereof (b-1) to the total content of an olefin sulfonic acid having 18 carbon atoms or a salt thereof (a-2) and a hydroxyalkanesulfonic acid having 18 carbon atoms or a salt thereof (b-2), ({(a-1)+(b-1)}/{(a-2)+(b-2)}), is preferably 0.5 or more and 5 or less, and more preferably from 1.3 to 4 in the total content of the component (A) and the component (B).

Further, from a viewpoint of further enhancing low temperature storage stability of the composition, the total content of an olefin sulfonic acid having 16 carbon atoms or a salt thereof (a-1), an olefin sulfonic acid having 18 carbon atoms or a salt thereof (a-2), a hydroxyalkanesulfonic acid having 16 carbon atoms or a salt thereof (b-1), and a hydroxyalkanesulfonic acid having 18 carbon atoms or a salt thereof (b-2) is preferably from 90 to 100 mass %, and furthermore preferably from 95 to 100 mass % in the total content of the component (A) and the component (B).

The sulfonic acid group of the component (A) can be located at position 1 or 2 of the olefin chain that is the main chain, or further located internally in the olefin chain, but from a viewpoint of effectively enhancing the adsorption of the component (C) on the tooth surface and securing the delivery of the component (C) to tooth surface, the component (A) preferably contains an olefin sulfonic acid having a sulfonic acid group at position 2 of an olefin chain or a salt thereof. Further, the sulfonic acid group of the component (B) can be similarly located at position 1 or 2 of the alkane chain that is the main chain, or further located internally in the alkane chain, but from a viewpoint of enhancing the adsorption of the component (C) on the tooth surface effectively by excellent delivery of the component (C) to the tooth surface, the component (B) preferably contains a hydroxyalkanesulfonic acid having a sulfonic acid group at position 2 of the alkane chain or a salt thereof.

Specifically, the total content of the olefin sulfonic acid having a sulfonic acid group at position 2 of the olefin chain or a salt thereof in the component (A) and the hydroxyalkanesulfonic acid having a sulfonic acid group at position 2 of the alkane chain or a salt thereof in the component (B) is preferably 5 mass % or more, more preferably 8 mass % or more, further preferably 10 mass % or more, and furthermore preferably 15 mass % or more, in the total content of the component (A) and the component (B) from a viewpoint of effectively enhancing the adsorption of the component (C) on tooth surfaces. Further, the total content of the olefin sulfonic acid having a sulfonic acid group at position 2 of the olefin chain or a salt thereof in the component (A) and the hydroxyalkanesulfonic acid having a sulfonic acid group at position 2 of the alkane chain or a salt thereof in the component (B) is preferably 30 mass % or less, and more preferably 25 mass % or less in the total content of the component (A) and the component (B) from a viewpoint of the delivery capacity of the component (C) to tooth surfaces, the composition stability and the productivity. Additionally, the total content of the olefin sulfonic acid having a sulfonic acid group at position 2 of the olefin chain or a salt thereof in the component (A) and the hydroxyalkanesulfonic acid having a sulfonic acid group at position 2 of the alkane chain or a salt thereof in the component (B) is preferably from 5 to 30 mass % more preferably from 8 to 30 mass %, further preferably from 10 to 25 mass %, and further preferably from 15 to 25 mass %, in the total content of the component (A) and the component (B).

Note that the contents of these olefin sulfonic acids having a sulfonic acid group at position 2 of the olefin chain or salts thereof, and the total content of these, all mean values in terms of acid, and the contents of the hydroxyalkanesulfonic acids having a sulfonic acid group at position 2 of the alkane chain or salts thereof, and the total content of these also mean the same.

The total content of the olefin sulfonic acid having a sulfonic acid group at position 1 of an olefin chain or a salt thereof in the component (A) and the hydroxyalkanesulfonic acid having a sulfonic acid group at position 1 of the alkane chain or a salt thereof in the component (B) is preferably 1 mass % or more, more preferably 1.5 mass % or more, further preferably 2 mass % or more, and further preferably 2.5 mass % or more, in the total content of the component (A) and the component (B) from a viewpoint of the delivery of the component (C) to the tooth surface, the composition stability and the productivity. Further, the total content of the olefin sulfonic acid having a sulfonic acid group at position 1 of the olefin chain or a salt thereof in the component (A) and the hydroxyalkanesulfonic acid having a sulfonic acid group at position 1 of the alkane chain or a salt thereof in the component (B) is preferably 20 mass % or less, more preferably 10 mass % or less, and further preferably 5 mass % or less, in the total content of the component (A) and the component (B) from a viewpoint of effectively enhancing the adsorption of the component (C) on the tooth surface. Additionally, the total content of the olefin sulfonic acid having a sulfonic acid group at position 1 of the olefin chain or a salt thereof of the component (A) and the hydroxyalkanesulfonic acid having a sulfonic acid group at position 1 of the alkane chain or a salt thereof of the component (B) is preferably from 1 to 20 mass %, more preferably from 1.5 to 10 mass %, further preferably from 2 to 5 mass %, and further preferably from 2.5 to 5 mass %, in the total content of the component (A) and the component (B).

Further, from a viewpoint of the composition stability and productivity, the component (A) and the component (B), preferably contain an olefin sulfonic acid having a sulfonic acid group at positions other than position 1 and 2 of the olefin chain or salts thereof, and a hydroxyalkanesulfonic acid having a sulfonic acid group at positions other positions 1 and 2 of the alkane chain or salts thereof, in addition to the above olefin sulfonic acid having a sulfonic acid group at position 1 of the olefin chain or a salt thereof, the hydroxyalkanesulfonic acid having a sulfonic acid group at position 1 of the alkane chain or a salt thereof, the olefin sulfonic acid having a sulfonic acid group at position 2 of the olefin chain or a salt thereof, and the hydroxyalkanesulfonic acid having a sulfonic acid group at position 2 of the alkane chain or a salt thereof.

Note that, the total content of the olefin sulfonic acid having a sulfonic acid group at position 1 of the olefin chain or a salt thereof in the component (A) and the hydroxyalkanesulfonic acid having a sulfonic acid group at position 1 of the alkane chain or a salt thereof in the component (B), or the total content of the olefin sulfonic acid having a sulfonic acid group at position 2 of the olefin chain or a salt thereof in the component (A) and the hydroxyalkanesulfonic acid having a sulfonic acid group at position 2 of the alkane chain or a salt thereof in the component (B) in the total content of the component (A) and the component (B) can be both determined based on a peak area ratio of each component obtained by using gas chromatography (GC).

Specifically, the components (A) and (B) are reacted with trimethylsilyldiazomethane to be methyl esterified derivatives and subsequently the components are separated by GC. Using a peak area ratio of each component as a mass ratio, the content of the internal olefin sulfonic acid having a sulfonic acid group at position 2 or a salt thereof is calculated. A system and analysis conditions used for the measurement are as follows.

GC System "Agilent Technology 6850" (manufactured by Agilent Technologies, Inc.), column "HP-1 capillary column" (30 m×320 μm×0.25 μm, manufactured by Agilent Technologies, Inc.), detector (hydrogen flame ionization detector (FID)), injection temperature 300° C., detector temperature 300° C., He flow rate 1.0 mL/min., oven (60° C. (0 min.)→10° C./min.→300° C. (10 min.).

The total content of the component (A) and the component (B), which are active components, in the oral composition of the present invention is 0.001 mass % or more, preferably 0.005 mass % or more, more preferably 0.01 mass % or more, and further preferably 0.02 mass % or more in the oral composition of the present invention, from a viewpoint of securing excellent adsorption of the component (C) on the tooth surface. Further, the total content of the component (A) and the component (B) is 2.5 mass % or less, preferably 1.3 mass % or less, more preferably 0.5 mass % or less, and further preferably 0.08 mass % or less in the oral composition of the present invention, from a viewpoint of the delivery of the component (C) to the tooth surface and inhibiting development of irritation and damages such as bitterness and astringency in the oral cavity when applied. Additionally, the total content of the component (A) and the component (B) is 0.001 mass % or more and 2.5 mass % or less, preferably from 0.005 to 1.3 mass %, more preferably from 0.01 to 0.5 mass %, and further preferably from 0.02 to 0.08 mass % in the oral composition of the present invention.

The component (A) and the component (B) can be obtained through steps of sulfonating a raw material olefin having 14 or more and 20 or less carbon atoms, then neutralizing, subsequently hydrolyzing, and then purifying the obtained hydrolysate.

There are no limitations on sulfonation, neutralization, or hydrolysis, and, for examples, the conditions described in JP-B-1633184, JP-B-2625150, and Tenside Surf. Det. 31(5) 299 (1994) can be referred. Further, various methods can be used as the step of purifying the hydrolysate obtained through the above hydrolysis, but the purification step preferably has a step of extracting the component (A) and the component (B) contained in an aqueous phase after separating an oil phase by adding a nonpolar solvent. Namely, specifically, the purification step includes a step of dispersing the hydrolysate obtained by hydrolysis in ethanol and adding a nonpolar solvent thereto, a step of subsequently separating an oil phase, and a step of further extracting the component (A) and the component (B) from the separated aqueous phase. For the above nonpolar solvent, one or more selected from the group consisting of petroleum ether, hexane, and toluene can be used. Further, the step of separating an oil phase may be carried out several times. Examples of the step of extracting the component (A) and the component (B) from the separated aqueous phase include a means of evaporating water and a means of removing deposits in the aqueous phase.

Note that a raw material olefin of the component (A) and a raw material olefin of the component (B) may be the same or different.

When the component (A) and the component (B) are obtained by sulfonating a raw material olefin, neutralizing, and hydrolyzing followed by extraction from an aqueous phase separated from an oil phase by adding a nonpolar solvent, the content of the olefin having a double bond at position 2 in the olefins which are raw materials of the component (A) and the component (B) is preferably the total of 10 mass % or more, more preferably 15 mass % or more, and further preferably 20 mass % or more, in the whole amount of raw material olefins of the component (A) and the component (B) from a viewpoint of effectively enhancing the adsorption of the component (C) on the tooth surface. Further, the content of the olefin having a double bond at position 2 in the raw material olefins of the component (A) and the component (B) is preferably the total of 50 mass % or less, more preferably 45 mass % or less, and further preferably 35 mass % or less, in the whole amount of raw material olefins of the component (A) and the component (B) from a viewpoint of securing the delivery of the component (C) to the tooth surface, reducing the production costs, and improving the productivity.

Further, from a viewpoint of furthermore enhancing the adsorption of the component (C) on the tooth surface and a viewpoint of adding improvement in foaming and foam quality, the content of the olefin having a double bond at position 1, so-called α-olefin, in the olefins which are raw materials of the component (A) and the component (B) is preferably the total of 5 mass % or less, more preferably 2 mass % or less, and the lower limit thereof 0.1 mass % or more, or 0.2 mass % or more, in the whole amount of raw material olefins of the component (A) and the component (B).

Note that the distribution of double bonds in the raw material olefins can be measured using, for example, a gas chromatography-mass spectrometry (abbreviated as GC-MS). Specifically, each of the components with different carbon chain lengths and the position of double bond position are precisely separated using a gas chromatography analyzer (hereinafter, abbreviated as GC) and subjected to a mass spectrometry (hereinafter, abbreviated as MS), respectively to identify the position of double bond thereof, and respective proportions thereof can be determined from GC peak areas thereof.

The above sulfonation reaction can be carried out by reacting 1.0 to 1.2 mol of a sulfur trioxide gas with 1 mol of a raw material olefin. The reaction is preferably carried out at a reaction temperature of 20 to 40° C. The neutralization is carried out by reacting an alkali aqueous solution such as sodium hydroxide, ammonia, or 2-aminoethanol in an amount of 1.0 to 1.5 molar times the theoretical value of the sulfonic acid group. The hydrolysis reaction can be carried out in the presence of water at 90 to 200° C. for 3 to 4 hours. These reactions can be sequentially carried out. After completion of the hydrolysis reaction, extraction removal of impurities and suitably washing are carried out to thereby purify the component (A) and the component (B).

In the oral composition of the present invention, the total content of anionic surfactants including the component (A) and the component (B) is preferably less than 3 mass %, more preferably 2.8 mass % or less, and further preferably 2.5 mass % or less, in the oral composition of the present invention from a viewpoint of inhibiting development of irritation and damage in the oral cavity when applied, and comfortable use by a user.

The oral composition of the present invention contains, as the component (C), one or more oil soluble active components selected from the group consisting of isopropyl methylphenol, triclosan, thymol, and β-glycyrrhetinic acid. In the present invention, oil soluble active components of the component (C) and the component (D) are used together with the above component (A) and the component (B) in a specific quantitative relation, whereby enabling enhancement in the delivery capacity of the component (C) to the tooth surface for effective and efficient adsorption of the component (C) on the tooth surface and demonstration of an excellent biofilm formation inhibitory effect. Of these, one or two selected from the group consisting of isopropyl methylphenol and triclosan are preferable from a viewpoint of securing an excellent biofilm formation inhibitory effect while securing favorable delivery of the component (C) together with the component (D).

From a viewpoint of securing excellent adsorption of the component (C) on the tooth surface to improve a biofilm formation inhibitory effect, the content of the component (C) is preferably 0.001 mass % or more, more preferably 0.003 mass % or more, further preferably 0.005 mass % or more, further preferably 0.008 mass % or more, and further preferably 0.015 mass % or more, in the oral composition of the present invention. Further, from a viewpoint of securing the delivery of the component (C) to the tooth surface and the composition stability, the content of the component (C) is preferably 1 mass % or less, more preferably 0.5 mass % or less, more preferably 0.1 mass % or less, and more preferably 0.08 mass % or less, in the oral composition of the present invention. Additionally, the content of the component (C) is preferably from 0.001 to 1 mass %, more preferably from 0.003 to 0.5 mass %, further preferably from 0.005 to 0.1 mass %, further preferably from 0.008 to 0.08 mass %, and further preferably from 0.015 to 0.08 mass % in the oral composition of the present invention.

From a viewpoint of securing the delivery capacity of the component (C) to the tooth surface, the mass ratio of the content of the component (C) to the total content of the component (A) and the component (B), ((C)/{(A)+(B)}), is preferably 0.01 or more, more preferably 0.1 or more, further preferably 0.2 or more, and further preferably 0.4 or more. Further, from a viewpoint of securing the excellent adsorption of the component (C) on the tooth surface and the composition stability, the mass ratio of the content of the component (C) to the total content of the component (A) and the component (B), ((C)/{(A)+(B)}), is preferably 6 or less, more preferably 5 or less, further preferably 3.5 or less, furthermore preferably 2 or less, and particularly preferably 0.9 or less. Additionally, the mass ratio of the content of the component (C) to the total content of the component (A) and the component (B), ((C)/{(A)+(B)}), is preferably from 0.01 to 6, more preferably from 0.01 to 5, further preferably from 0.1 to 3.5, further preferably from 0.2 to 2, and further preferably from 0.4 to 0.9.

The oral composition of the present invention contains a water-soluble alkali metal salt as the component (D). Inclusion of the component (D), together with the component (A), the component (B), and the component (C), presumably forms a vesicle-like structure, and it is considered that this contributes to improvement of the delivery of the component (C) to the tooth surface to thereby contribute to development of excellent adsorption of the component (C).

From a viewpoint of effectively enhancing the delivery capacity of the component (C) to the tooth surface, the component (D) specifically is preferably one or more selected from the group consisting of a calcium salt, a magnesium salt, and a strontium salt, and more preferably a calcium salt or a magnesium salt. More specifically, examples thereof include one or more selected from the group consisting of calcium chloride, calcium lactate, calcium hypophosphite, calcium hydroxide, calcium nitrite, calcium nitrate, calcium carbonate, magnesium chloride, magnesium sulfate, magnesium nitrate, and magnesium carbonate. Of these, calcium chloride or magnesium chloride is preferable, and calcium chloride is more preferable.

From a viewpoint of securing the excellent delivery capacity of the component (C) to the tooth surface, the content of the component (D) in terms of salt is preferably 0.001 mass % or more, more preferably 0.003 mass % or more, further preferably 0.006 mass % or more, and further preferably 0.008 mass % or more, in the oral composition of the present invention. Further, from a viewpoint of securing the composition stability, the content of the component (D) in term of salt is preferably 1 mass % or less, more preferably 0.1 mass % or less, further preferably 0.05 mass % or less, and further preferably 0.03 mass % or less, in the oral composition of the present invention. Additionally, the content of the component (D) in terms of salt in the oral composition of the present invention is preferably from 0.001 to 1 mass %, more preferably from 0.003 to 0.1 mass %, further preferably from 0.006 to 0.05 mass %, and further preferably from 0.008 to 0.03 mass %.

From a viewpoint of securing excellent delivery of the component (C) to tooth surface and enhancing a biofilm formation inhibitory effect, the mass ratio of the content of the component (C) to the content of the component (D), ((C)/(D)), is preferably 0.05 or more, more preferably 0.1 or more, further preferably 0.4 or more, further preferably 0.7 or more, and further preferably 1.5 or more. Further, from a viewpoint of securing the composition stability, the mass ratio of the content of the component (C) to the content of the component (D), ((C)/(D)), is preferably 20 or less, more preferably 10 or less, further preferably 5 or less, and further preferably 2.5 or less. Additionally, the mass ratio of the content of the component (C) to the content of the component (D), ((C)/(D)), is preferably from 0.05 to 20, more preferably from 0.1 to 20, further preferably from 0.4 to 10, further preferably from 0.7 to 5, and further preferably from 1.5 to 2.5.

From a viewpoint of securing the excellent adsorption of the component (C) on the tooth surface, the mass ratio of the content of the component (D) to the total content of the component (A) and the component (B), ((D)/{(A)+(B)}), is preferably 0.01 or more, more preferably 0.1 or more, and further preferably 0.2 or more. Further, from a viewpoint of securing the composition stability, the mass ratio of the content of the component (D) to the total content of the component (A) and the component (B), ((D)/{(A)+(B)}), is preferably 10 or less, more preferably 5 or less, and further preferably 1 or less. Additionally, the mass ratio of the content of the component (D) to the total content of the component (A) and the component (B), ((D)/{(A)+(B)}), is preferably from 0.01 to 10, more preferably from 0.1 to 5, and further preferably from 0.2 to 1.

The form of the oral composition of the present invention is not particularly limited as long as it is applicable in the mouth, and the composition can be used as a liquid oral composition such as a mouthwash and a liquid toothpaste or a toothpaste composition such as a toothpaste and a tooth powder. Of these, a liquid oral composition selected from the group consisting of a mouthwash and a liquid toothpaste is preferable from a viewpoint of effectively forming a vesicle-like structure by inclusion of the component (D) together with the component (A), the component (B), and the component (C) and contributing to improvement in the delivery of the component (C) to the tooth surface.

The oral composition of the present invention contains water in addition to the above components. Due to this, the component (A) to the component (D) are favorably spread in the oral cavity while dissolved or dispersed, to thereby promote the delivery and the adsorption of the component (C) on the tooth surface.

The content of water is preferably 3 mass % or more, more preferably 5 mass % or more, and further preferably 10 mass % or more, and preferably 99 mass % or less, more preferably 97 mass % or less, and further preferably 95 mass % or less in the oral composition of the present invention.

More specifically, for example, when the oral composition of the present invention is a liquid oral composition, the content of water is preferably 50 mass % or more, more preferably 70 mass % or more, and further preferably 80 mass % or more in 100 mass % of the liquid oral composition of the present invention. The content of water is the balance of other components, and preferably 99 mass % or less, more preferably 97 mass % or less, further preferably less than 95 mass % in 100 mass % of the liquid oral composition of the present invention. Further, when the oral composition of the present invention is a toothpaste composition, the content of water is preferably 3 mass % or more, more preferably 10 mass % or more, and preferably 65 mass % or less, more preferably 40 mass % in 100 mass % of the toothpaste composition of the present invention.

When the oral composition of the present invention is a toothpaste composition, the amount of water therein can be determined by calculation from the amount of water mixed and the amount of water in the components mixed. For example, the amount of water can be measured using a Karl Fischer moisture titrator. For example, a trace level water content measurement apparatus (Hiranuma Inc.) can be used as Karl Fischer moisture titrator. With this apparatus, 5 g of a toothpaste composition is weighed, and suspended in 25 g of anhydrous methanol, and 0.02 g of the suspension is separately collected to measure an amount of water.

The oral composition of the present invention preferably contains sorbitol from a viewpoint of inhibiting discomforts caused by development of irritation of tingling sensation and damage in the oral cavity due to the component (A), the component (B), the component (C), and the component (D) and providing a favorable flavor while securing the composition stability. From a viewpoint of inhibiting discomforts and providing a favorable flavor, the content of sorbitol is, preferably 2 mass % or more, more preferably 4 mass % or more, and further preferably 5 mass % or more, in the oral composition of the present invention. Further, from a viewpoint of providing a fresh feel upon use and taste, the content of sorbitol is, preferably 60 mass % or less, more preferably 50 mass % or less, further preferably 40 mass % or less, and furthermore preferably 30 mass % or less, in the oral composition of the present invention. Further, when the oral composition of the present invention is a liquid oral composition, the content of sorbitol is preferably 15 mass % or less, more preferably 10 mass % or less, and further preferably 7 mass % or less, in the oral composition of the present invention. Additionally, the content of sorbitol is preferably from 2 to 60 mass %, more preferably from 4 to 50 mass %, further preferably from 5 to 40 mass %, and further preferably from 5 to 30 mass % in the oral composition of the present invention. Further, when the oral composition of the present invention is a liquid oral composition, the content of sorbitol is preferably from 2 to 15 mass %, more preferably from 4 to 10 mass %, and further preferably from 4 to 7 mass %, in the oral composition of the present invention.

The mass ratio of the content of sorbitol to the total content of the component (A) and the component (B), (sorbitol/{(A)+(B)}), is preferably 10 or more, more preferably 100 or more, and further preferably 150 or more from a viewpoint of securing the composition stability. Further, the mass ratio of the content of sorbitol to the total content of the component (A) and the component (B), (sorbitol/{(A)+(B)}), is preferably 2,000 or less, more preferably 800 or less, and further preferably 400 or less from a viewpoint of securing the excellent adsorption of the component (C) on the tooth surface. Additionally, the mass ratio of the content of sorbitol to the total content of the component (A) and the component (B), (sorbitol/{(A)+(B)}), is preferably 10 or more and 2,000 or less, more preferably from 100 to 800, and further preferably from 150 to 400.

When in the form of a toothpaste composition, the oral composition of the present invention can further contains a binder such as sodium alginate, sodium carboxymethylcellulose, carrageenan, xanthan gum, sodium polyacrylate, hydroxyethyl cellulose, hydroxypropyl cellulose, pectin, tragacanth gum, gum arabic, guar gum, karaya gum, locust bean gum, gellan gum, tamarind gum, psyllium seed gum, polyvinyl alcohol, sodium chondroitin sulfate, and a methoxyethylene maleic anhydride copolymer; thickening silica (oil absorption measured by the method in accordance with JIS K5101-13-2 is from 200 to 400 mL/100 g); and an abrasive such as calcium phosphate, calcium hydrogen phosphate, calcium carbonate, aluminum hydroxide, aluminum silicate, zirconium silicate, and abrasive silica (oil absorption measured by the method in accordance with JIS K5101-13-2 is from 50 to 150 mL/100 g).

The pH of the oral composition of the present invention at 25° C. is preferably 6 or more, more preferably 6.5 or more, and further preferably 7 or more from a viewpoint of effectively forming a vesicle-like structure by inclusion of the component (D) together with the component (A), the component (B), and the component (C) and contributing to improvement of the delivery of the component (C) to the tooth surface. Further, the pH of the oral composition of the present invention at 25° C. is preferably 11 or less, preferably 10 or less, and more preferably 9.5 or less from a viewpoint of preventing damages. Additionally, the pH of the oral composition of the present invention at 25° C. is preferably from 6 to 11, more preferably from 6.5 to 10, and further preferably from 7 to 9.5.

Note that the pH of the oral composition of the present invention is a value measured at 25° C. using a pH electrode, and when the oral composition of the present invention is a toothpaste composition, such a pH means a value measured after the composition is prepared into an aqueous solution having a concentration of 10 mass % using ion-exchange water.

The oral composition of the present invention can further contain, within a range in which the effects of the present invention are not affected, a surfactant other than the component (A) and the component (B); a fluoride ion-supplying compound such as sodium fluoride, potassium fluoride, and ammonium fluoride, and a fluorine-containing compound such as sodium monofluorophosphate; a wetting agent such as glycerin, polyethylene glycol, and propylene glycol; a sweetener; a perfume; a pH adjusting agent; and other active components.

From a viewpoint of effectively enhancing the adsorption of the component (C) on the tooth surface and demonstrating an excellent biofilm formation inhibitory effect, the oral composition of the present invention is most preferably an oral composition which comprises the following components (A) to (E):

(A) an olefin sulfonic acid having 14 or more and 20 or less carbon atoms or a salt thereof, (B) a hydroxyalkanesulfonic acid having 14 or more and 20 or less carbon atoms or a salt thereof, (C) 0.001 to 1 mass % of one or more oil soluble active components selected from the group consisting of isopropyl methylphenol, triclosan, thymol, and β-glycyrrhetinic acid, (D) a water-soluble alkali metal salt, and (E) water, wherein the total content of the component (A) and the component (B) is 0.005 mass % or more and 1.3 mass % or less in the composition, and the content of the component (A) is 3 mass % or more and 50 mass % or less in the total content of the component (A) and the component (B), and the total content of an olefin sulfonic acid having 18 carbon atoms or a salt thereof (a-2) and a hydroxyalkanesulfonic acid having 18 carbon atoms or a salt thereof (b-2) is from 90 to 100 mass % in the total content of the component (A) and the component (B), the mass ratio of the content of the component (C) to the total content of the component (A) and the component (B), ((C)/{(A)+(B)}), is 0.1 or more and 3 or less, the mass ratio of the content of the component (D) to the total content of the component (A) and the component (B), ((D)/{(A)+(B)}), is 0.01 or more and 10 or less, and the mass ratio of the content of the component (C) to the content of the component (D), ((C)/(D)), is 0.1 or more and 20 or less.

From a viewpoint of effectively maintaining the adsorption of the component (C) on the tooth surface and furthermore enhancing foaming and foam densifying property, the oral composition of the present invention is most preferably an oral composition which comprises the following components (A) to (E):

(A) an olefin sulfonic acid having 14 or more and 20 or less carbon atoms or a salt thereof, (B) a hydroxyalkanesulfonic acid having 14 or more and 20 or less carbon atoms or a salt thereof, (C) 0.001 to 1 mass % of one or more oil soluble active components selected from the group consisting of isopropyl methylphenol, triclosan, thymol, and β-glycyrrhetinic acid, (D) a water-soluble alkali metal salt, and (E) water, wherein the total content of the component (A) and the component (B) is 0.005 mass % or more and 1.3 mass % or less in the composition, and the content of the component (A) is 3 mass % or more and 50 mass % or less in the total content of the component (A) and the component (B), and the total content of an olefin sulfonic acid having 16 carbon atoms or a salt thereof (a-1) and a hydroxyalkanesulfonic acid having 16 carbon atoms or a salt thereof (b-1) is from 90 to 100 mass % in the total content of the component (A) and the component (B), the mass ratio of the content of the component (C) to the total content of the component (A) and the component (B), ((C)/{(A)+(B)},) is 0.1 or more and 3 or less, the mass ratio of the content of the component (D) to the total content of the component (A) and the component (B), ((D)/{(A)+(B)}), is 0.01 or more and 10 or less, and the mass ratio of the content of the component (C) to the content of the component (D), ((C)/(D)), is 0.1 or more and 20 or less.

From a viewpoint of effectively maintaining the adsorption of the component (C) on the tooth surface and realizing more excellent low temperature storage stability of the composition, the oral composition of the present invention is most preferably an oral composition which comprises the following components (A) to (E):

(A) an olefin sulfonic acid having 14 or more and 20 or less carbon atoms or a salt thereof, (B) a hydroxyalkanesulfonic acid having 14 or more and 20 or less carbon atoms or a salt thereof, (C) 0.001 to 1 mass % of one or more oil soluble active components selected from the group consisting of isopropyl methylphenol, triclosan, thymol, and β-glycyrrhetinic acid, (D) a water-soluble alkali metal salt, and (E) water, wherein the total content of the component (A) and the component (B) is 0.005 mass % or more and 1.3 mass % or less in the composition, and the content of the component (A) is 3 mass % or more and 50 mass % or less in the total content of the component (A) and the component (B), and the total content of an olefin sulfonic acid having 16 carbon atoms or a salt thereof (a-1), an olefin sulfonic acid having 18 carbon atoms or a salt thereof (a-2), a hydroxyalkanesulfonic acid having 16 carbon atoms or a salt thereof (b-1), and a hydroxyalkanesulfonic acid having 18 carbon atoms or a salt thereof (b-2) is from 90 to 100 mass % in the total content of the component (A) and the component (B), and in the total content of the component (A) and the component (B), the mass ratio of the total content of the component (a-1) and the component (b-1) to the total content of the component (a-2) and the component (b-2), ({(a-1)+(b-1)}/{(a-2)+(b-2)}), is 0.5 or more and 5 or less, the mass ratio of the content of the component (C) to the total content of the component (A) and the component (B), ((C)/{(A)+(B)}), is 0.1 or more and 3 or less, the mass ratio of the content of the component (D) to the total content of the component (A) and the component (B), ((D)/{(A)+(B)}), is 0.01 or more and 10 or less, and the mass ratio of the content of the component (C) to the content of the component (D), ((C)/(D)), is 0.1 or more and 20 or less.

The present invention, with respect to the above-described embodiments, further discloses the following oral compositions.

[1] An oral composition comprising the following components (A), (B), (C), and (D):

(A) an olefin sulfonic acid having 14 or more and 20 or less carbon atoms or a salt thereof, (B) a hydroxyalkanesulfonic acid having 14 or more and 20 or less carbon atoms or a salt thereof, (C) one or more oil soluble active components selected from the group consisting of isopropyl methylphenol, triclosan, thymol, and β-glycyrrhetinic acid, and (D) a water-soluble alkali metal salt, wherein the total content of the component (A) and the component (B) is 0.001 mass % or more and 2.5 mass % or less, and the content of the component (A) is 3 mass % or more and 50 mass % or less in the total content of the component (A) and the component (B).

[2] The oral composition of the above [1], wherein the olefin sulfonic acid or a salt thereof of the component (A) has preferably 16 or more and preferably 18 or less carbon atoms.

[3] The oral composition of the above [1] or [2], wherein the hydroxyalkanesulfonic acid or a salt thereof of the component (B) has preferably 16 or more and preferably 18 or less carbon atoms.

[4] The oral composition of any one of the above [1] to [3], wherein the total content of an olefin sulfonic acid having 18 carbon atoms or a salt thereof (a-2) and a hydroxyalkanesulfonic acid having 18 carbon atoms or a salt thereof (b-2) is preferably from 50 to 100 mass %, more preferably from 70 to 100 mass %, further preferably from 90 to 100 mass %, and further preferably from 95 to 100 mass % in the total content of the component (A) and the component (B).

[5] The oral composition of any one of the above [1] to [3], wherein the total content of an olefin sulfonic acid having 16 carbon atoms or a salt thereof (a-1) and a hydroxyalkanesulfonic acid having 16 carbon atoms or a salt thereof (b-1) is preferably from 90 to 100 mass %, and more preferably from 95 to 100 mass % in the total content of the component (A) and the component (B).

[6] The oral composition of any one of the above [1] to [5], wherein the content of the above (A) is preferably 45 mass % or less, more preferably 30 mass % or less, further preferably 25 mass % or less, and further preferably 20 mass % or less, and preferably 5 mass % or more, more preferably 7 mass % or more, further preferably 9 mass % or more, and further preferably 10 mass % or more in the total content of the component (A) and the component (B).

[7] The oral composition of any one of the above [1] to [6], wherein the mass ratio of the total content of the olefin sulfonic acid having 16 carbon atoms or a salt thereof (a-1) and the hydroxyalkanesulfonic acid having 16 carbon atoms or a salt thereof (b-1) to the total content of the olefin sulfonic acid having 18 carbon atoms or a salt thereof (a-2) and the hydroxyalkanesulfonic acid having 18 carbon atoms or a salt thereof (b-2), ({(a-1)+(b-1)}/{(a-2)+(b-2)}), is preferably 0.5 or more and 5 or less, and more preferably from 1.3 to 4 in the total content of the component (A) and the component (B).

[8] The oral composition of any one of the above [1] to [7], wherein the total content of the olefin sulfonic acid having 16 carbon atoms or a salt thereof (a-1), the olefin sulfonic acid having 18 carbon atoms or a salt thereof (a-2), the hydroxyalkanesulfonic acid having 16 carbon atoms or a salt thereof (b-1), and the hydroxyalkanesulfonic acid having 18 carbon atoms or a salt thereof (b-2) is preferably from 90 to 100 mass %, and furthermore preferably from 95 to 100 mass % in the total content of the component (A) and the component (B).

[9] The oral composition of any one of the above [1] to [8], wherein the total content of an olefin sulfonic acid having a sulfonic acid group at position 2 of an olefin chain or a salt thereof in the component (A) and a hydroxyalkanesulfonic acid having a sulfonic acid group at position 2 of an alkane chain or a salt thereof in the component (B) is preferably 5 mass % or more, more preferably 8 mass % or more, further preferably 10 mass % or more, and further preferably 15 mass % or more, and preferably 30 mass % or less, and more preferably 25 mass % or less in the total content of the component (A) and the component (B).

[10] The oral composition of any one of the above [1] to [9], wherein the total content of an olefin sulfonic acid having a sulfonic acid group at position 1 of an olefin chain or a salt thereof in the component (A) and a hydroxyalkanesulfonic acid having a sulfonic acid group at position 1 of an alkane chain or a salt thereof in the component (B) is preferably 1 mass % or more, more preferably 1.5 mass % or more, further preferably 2 mass % or more, and further preferably 2.5 mass % or more, and preferably 20 mass % or less, more preferably 10 mass % or less, and further preferably 5 mass % or less in the total content of the component (A) and the component (B).

The oral composition of any one of the above [1] to [10], wherein the total content of the component (A) and the component (B) is preferably 0.005 mass % or more, more preferably 0.01 mass % or more, and further preferably 0.02 mass % or more, and preferably 1.3 mass % or less, more preferably 0.5 mass % or less, and further preferably 0.08 mass % or less.

The oral composition of any one of the above [1] to [11], wherein the content of an olefins having a double bond at position 1 in olefins of raw materials of the component (A) and the component (B) is preferably the total of 5 mass % or less, more preferably 2 mass % or less, and the lower limit thereof is 0.1 mass % or more, or 0.2 mass % or more, in the whole amount of raw material olefins of the component (A) and the component (B).

[13] The oral composition of any one of the above [1] to [12], wherein the total content of an anionic surfactant comprising the component (A) and the component (B) is preferably 3 mass % or less, more preferably 2.8 mass % or less, and further preferably 2.5 mass % or less.

[14] The oral composition of any one of the above [1] to [13], wherein the content of the component (C) is preferably 0.001 mass % or more, more preferably 0.003 mass % or more, further preferably 0.005 mass % or more, further preferably 0.008 mass % or more, and further preferably 0.015 mass % or more, and preferably 1 mass % or less, more preferably 0.5 mass % or less, more preferably 0.1 mass % or less, and more preferably 0.08 mass % or less.

[15] The oral composition of any one of the above [1] to [14], wherein the mass ratio of the content of the component (C) to the total content of the component (A) and the component (B), ((C)/{(A)+(B)}), is preferably 0.01 or more, more preferably 0.1 or more, further preferably 0.2 or more, and further preferably 0.4 or more, and preferably 6 or less, more preferably 5 or less, further preferably 3.5 or less, further preferably 2 or less, and further preferably 0.9 or less. [16] The oral composition of any one of the above [1] to [15], wherein the component (D) is preferably one or more selected from the group consisting of a calcium salt, a magnesium salt, and a strontium salt, and more preferably a calcium salt or a magnesium salt.

[17] The oral composition of any one of the above [1] to [16], wherein the content of the component (D) in terms of salt is preferably 0.001 mass % or more, more preferably 0.003 mass % or more, further preferably 0.006 mass % or more, and further preferably 0.008 mass % or more, and preferably 1 mass % or less, more preferably 0.1 mass % or less, further preferably 0.05 mass % or less, and further preferably 0.03 mass % or less.

[18] The oral composition of any one of the above [1] to [17], wherein the mass ratio of the content of the component (C) to the content of the component (D), ((C)/(D)), is preferably 0.05 or more, more preferably 0.1 or more, further preferably 0.4 or more, further preferably 0.7 or more, and further preferably 1.5 or more, and preferably 20 or less, more preferably 10 or less, further preferably 5 or less, and further preferably 2.5 or less.

[19] The oral composition of any one of the above [1] to [18], wherein the mass ratio of the content of the component (D) to the total content of the component (A) and the component (B), ((D)/{(A)+(B)}), is preferably 0.01 or more, more preferably 0.1 or more, and further preferably 0.2 or more, and preferably 10 or less, more preferably 5 or less, and further preferably 1 or less.

[20] The oral composition of any one of the above [1] to [19], wherein the content of water is preferably 3 mass % or more, more preferably 5 mass % or more, and further preferably 10 mass % or more, and preferably 99 mass % or less, more preferably 97 mass % or less, and further preferably 95 mass % or less.

[21] The oral composition of any one of the above [1] to [20], wherein the content of sorbitol is preferably 2 mass % or more, more preferably 4 mass % or more, and further preferably 5 mass % or more, and preferably 60 mass % or less, more preferably 50 mass % or less, further preferably 40 mass % or less, and further preferably 30 mass % or less.

[22] The oral composition of any one of the above [1] to [21], wherein the mass ratio of the content of sorbitol to the total content of the component (A) and the component (B), (sorbitol/{(A)+(B)}), is preferably 10 or more, more preferably 100 or more, and further preferably 150 or more, and preferably 2,000 or less, more preferably 800 or less, and further preferably 400 or less.

EXAMPLE

Hereinafter, the present invention is specifically described with reference to Examples. Note that a content of each component in the tables shows mass % unless otherwise specified.

Note that, for each of the physical properties, the following methods were used.

«Measurement Method of Double Bond Position in Raw Material Olefin»

The position of double bond of a raw material olefin was measured by gas chromatography (hereinafter, abbreviated as GC). Specifically, a raw material olefin was reacted with dimethyl disulphide to be a dithionated derivative and subsequently each of the components was separated by GC. The position of double bond of the raw material olefin was determined using each peak area.

Note that the system and analysis conditions used for the measurement are as follows. GC System (product name: HP6890, manufactured by HEWLETT PACKARD Company), column (product name: Ultra-Alloy-1HT capillary column 30 m×250 μm×0.15 μm, manufactured by Frontier Laboratories Ltd.), detector (hydrogen flame ionization detector (FID)), injection temperature 300° C., detector temperature 350° C., He flow rate 4.6 mL/min.

«Measurement Method of Content of Component (A) in Total Content of Component (A) (Olefin Compound) and Component (B) (Hydroxy Compound)»

The content of the component (A) was measured by HPLC-MS. Specifically, the hydroxy compound and olefin compound were separated by HPLC and the olefin compound was identified through MS. A proportion of the olefin compound was determined from the HPLC-MS peak area.

Note that a system and analysis conditions used for the measurement are as follows. HPLC system (product name: Agilent Technology 1100, manufactured by Agilent Technologies, Inc.), column (product name: L-column ODS 4.6×150 mm, manufactured by Chemical Evaluation and Research Institute, Japan), sample preparation (diluted 1,000-fold with methanol), eluent A (10 mM ammonium acetate added water), eluent B (10 mM ammonium acetate added methanol), gradients (0 min. (A/B=30/70%)→10 min. (30/70%)→55 min. (0/100%)→65 min. (0/100%)→66 min. (30/70%)→75 min. (30/70 h)), MS system (product name: Agilent Technology 1100 MS SL (G1946D)), MS detection (anion detection m/z60-1600, UV 240 nm).

«Measurement Method of Contents of Olefin Sulfonic Acid or Salt Thereof, and Hydroxyalkanesulfonic Acid or Salt Thereof Each Having a Sulfonic Acid Group at Position 2»

The binding position of the sulfonic acid group was measured by GC. Specifically, an olefin sulfonate and a hydroxyalkanesulfonate were reacted with trimethylsilyldiazomethane to be methyl esterified derivatives and subsequently each of the components was separated by GC. Using each peak area ratio as a mass ratio, the contents of the olefin sulfonic acid or a salt thereof, and the hydroxyalkanesulfonic acid or a salt thereof each having a sulfonic acid group at position 2 were calculated, and the contents in the total content of the component (A) and the component (B) were determined.

Note that a system and analysis conditions used for the measurement are as follows. GC System (product name: Agilent Technology 6850, (manufactured by Agilent Technologies, Inc.), column (product name: HP-1 capillary column 30 μm×320 μm×0.25 μm, manufactured by Agilent Technologies, Inc.), detector (hydrogen flame ionization detector (FID)), injection temperature 300° C., detector temperature 300° C., He flow rate 1.0 mL/min., oven (60° C. (0 min.)→10° C. /min.→300° C. (10 min.).

Production Example A: Synthesis of 31.3 Mass % of Raw Material Olefin Having 18 Carbon Atoms and Double Bond at Position 2

To a stirrer-equipped flask, 7,000 g (25.9 mol) of 1-octadecanol (product name: KALCOL 8098, produced by Kao Corporation) and 700 g (10 mass % relative to the raw material alcohol) of γ-alumina (STREM Chemicals, Inc.) as a solid acid catalyst were charged, and the reaction was carried out for 10 hours while circulating nitrogen (7,000 mL/min.) in the system at 280° C. under stirring. The alcohol conversion rate after completion of the reaction was 100%, and the purity of the raw material olefin having 18 carbon atoms (C18) was 98.2%. The obtained crude raw material olefin was transferred to a distillation flask and distilled at 148 to 158° C./0.5 mmHg to thereby obtain a purified raw material olefin having an olefin purity of 100%. The double bond distribution of the obtained raw material olefin was 0.8 mass % at C1 position, 31.3 mass % at C2 position, 22.9 mass % at C3 position, 15.5 mass % at C4 position, 10.8 mass % at C5 position, 7.2 mass % at C6 position, 5.3 mass % at C7 position, and the total of 6.2 mass % at C8, 9 positions.

Production Example B: Synthesis of 30.4 Mass % of Raw Material Olefin Having 16 Carbon Atoms and Double Bond at Position 2

To a stirrer-equipped flask, 7,000 g (28.9 mol) of 1-hexadecanol (product name: KALCOL 6098, produced by Kao Corporation) and 700 g (10 mass % relative to the raw material alcohol) of γ-alumina (STREM Chemicals, Inc.) as a solid acid catalyst were charged, and the reaction was carried out for 3 hours while circulating nitrogen (7,000 mL/min.) in the system at 280° C. under stirring. The alcohol conversion rate after completion of the reaction was 100%, and the purity of the raw material olefin having 16 carbon atoms (C16) was 99.6%. The obtained crude raw material olefin was transferred to a distillation flask and distilled at 136 to 160° C./4.0 mmHg to thereby obtain a purified C16 raw material olefin having an olefin purity of 100%. The double bond distribution of the obtained raw material olefin was 1.8 mass % at C1 position, 30.4 mass % at C2 position, 23.9 mass % at C3 position, 16.8 mass % at C4 position, 12.0 mass % at C5 position, 7.4 mass % at C6 position, and the total of 7.8 mass % at C7, 8 positions.

Production Example C: Synthesis of 27.8 Mass % of Raw Material Olefin Having 16/18 (Mass Ratio 79.4/20.6) Carbon Atoms and Double Bond at Position 2

A raw material olefin having 16 carbon atoms (C16) (double bond distribution was 0.5 mass % at C1 position, 30.1 mass % at C2 position, 25.5 mass % at C3 position, 18.9 mass % at C4 position, 11.1 mass % at C5 position, 7.0 mass % at C6 position, and the total of 7.0 mass % at C7, 8 positions) was obtained using the same method as in Production Example A and suitably adjusting reaction time.

Further, a raw material olefin having 18 carbon atoms (C18) (double bond distribution was 0.3 mass % at C1 position, 19.0 mass % at C2 position, 17.6 mass % at C3 position, 17.4 mass % at C4 position, 14.9 mass % at C5 position, 12.3 mass % at C6 position, 8.8 mass % at C7 position, and the total of 9.8 mass % at C8, 9 positions) was obtained using the same method as in Production Example B and suitably adjusting reaction time.

11.9 kg of the obtained C16 raw material olefin and 3.1 kg of the C18 raw material olefin were mixed to obtain 15.0 kg of a C16/18 (mass ratio 79.4/20.6) raw material olefin. The double bond distribution of this raw material olefin was 0.4 mass % at C1 position, 27.8 mass % at C2 position, 23.9 mass % at C3 position, 18.6 mass % at C4 position, 11.9 mass % at C5 position, 8.1 mass % at C6 position, 4.6 mass % at C7 position, 3.8 mass % at C8 position, and 1.0 mass % at C9 position.

Production Example I: Production of C18 Component (A) and Component (B)

The raw material olefin of C18 (the content of the raw material olefin having double bond at position 2 is 31.3 mass %) obtained in Production Example A was put in a thin film sulfonation reactor having an external jacket, and the sulfonation reaction was carried out using a sulfur trioxide gas under a condition of passing cooling water of 20° C. through the external jacket of the reactor. The molar ratio of $SO_3$/raw material olefin during the sulfonation reaction was set to 1.09. The obtained sulfonated product was added to an alkali aqueous solution prepared with sodium hydroxide in an amount of 1.5 molar times the theoretical acid value and neutralized at 30° C. for 1 hour with stirring. The neutralized product was hydrolyzed by heating in an autoclave at 160° C. for 3.5 hours to thereby obtain the C18 component (A) and component (B) of C18 as a crude product. 300 g of the crude product were transferred to a separatory funnel, 300 mL of ethanol was added thereto, and subsequently 300 mL of petroleum ether was added each time to extract and remove oil soluble impurities. During this operation, inorganic compounds (main component is mirabilite) deposited on the oil-water interface by addition of ethanol were also separated and remover from the aqueous phase by oil water separation operation. This extraction and removal operations were carried out three times. Subsequently, the aqueous phase was evaporated to dryness to thereby obtain the C18 component (A) and component (B).

The content of the component (A) was 10 mass % in the whole amount of the obtained component (A) and component (B). Further, the content of the remaining raw material olefin was less than 100 ppm (less than the lower detection limit of GC) and the content of inorganic compounds was 0.9 mass % in the whole amount of the obtained component (A) and component (B). Further, the total content of the olefin sulfonate having a sulfonic acid group at position 2 and the alkanesulfonate having a sulfonic acid group at position 2 was 21.4 mass % in the whole amount of the component (A) and the component (B).

Production Example II: Production of C16 Component (A) and Component (B)

The C16 component (A) and component (B) were obtained from the internal olefin of C16 (the content of the raw material olefin having double bond at position 2 is 30.4 mass %) obtained in Production Example B under the same conditions as in Production Example I.

The content of the component (A) was 10 mass % in the whole amount of the obtained component (A) and component (B). Further, the content of the remaining raw material internal olefin was less than 100 ppm (less than the lower detection limit of GC) and the content of inorganic compounds was 1.9 mass % in the whole amount of the component (A) and the component (B). Further, the total content of the olefin sulfonate having a sulfonic acid group at position 2 and the alkanesulfonate having a sulfonic acid group at position 2 was 20.3 mass % in the whole amount of the component (A) and the component (B).

Production Example III: Production of C16/18 Component (A) and Component (B)

Using the C16/18 raw material olefin (the content of the raw material olefin having double bond at position 2 was 27.8 mass %) obtained in Production Example C as a starting material, the C16/18 component (A) and component (B) were obtained by the same method as in Production Example I. The content of the component (A) in the whole amount of the obtained component (A) and component (B) was 14 mass %. Further, the content of the remaining raw material olefin was less than 100 ppm (less than the lower detection limit of GC) and the content of inorganic compounds was 1.2 mass % in the whole amount of the component (A) and the component (B). Further, the total content of the olefin sulfonate having a sulfonic acid group at position 2 and the alkanesulfonate having a sulfonic acid group at position 2 was 17.6 mass % in the whole amount of the component (A) and the component (B).

Physical properties of each of the component (A) and the component (B) obtained in the above Production Examples I to III are shown in Table 1.

TABLE 1

| Production Example | | | I | II | III |
|---|---|---|---|---|---|
| Raw material olefin | Content of olefin having double bond at position 1 (%) | | 0.8 | 1.8 | 0.4 |
| | Content of olefin having double bond at position 2 (%) | | 31.3 | 30.4 | 27.8 |
| Component (A) and component (B) | Number of carbon atoms | | C18 | C16 | C16/C18[1] |
| | Content of component (A) in whole amount (mass %) | | 20 | 10 | 14 |
| | Total content of hydroxy compound and olefin compound each having sulfonic acid group at position 1 in whole amount (mass %) | | — | — | 2.9 |
| | Total content of hydroxy compound and olefin compound each having sulfonic acid group at position 2 in whole amount ((mass %) | | 21.4 | 20.3 | 17.6 |

[1]Mass ratio of C16/C18 = 79.4/20.6

Examples 1 to 16, Comparative Examples 1 to 4

Each of the composition was prepared according to the formulations shown in Tables 2 and 3. Subsequently, each of the evaluations was carried out according to the following test methods using each of the obtained compositions.

The results are shown in Tables 2 and 3.

«Adsorption Test of Component (C) on Tooth Surface»

Hydroxyapatite (HA) powder (Taihei Chemical Industrial Co., Ltd.; hereinafter abbreviated as HA), the main component of enamel, was used as a tooth surface model. 10 mg of HA was immersed for 30 seconds in 1 mL of each composition component shown in Table 2, then washed with 2 mL of ion-exchange water, and a bactericide adsorbed on HA was extracted with a 65% acetonitrile solution and quantitatively determined using high performance liquid chromatography (ODS column: Superspher 100 (manufactured by: Kanto Chemical Co., Inc.), flow rate: 1 mL/min, measurement wavelength: 210 nm) to thereby calculate an adsorbed amount ($\mu mol/cm^2$). Note that when in the form of a tooth paste, the composition is diluted 4-fold with ion-exchange water and used for the test.

«Evaluation of Biofilm Formation Inhibitory Effects»

1) Treatment Using the Compositions

One surface of HAp substrates (manufactured by Cosmo Bio Co., Ltd., 1-cm square) was mirror-polished using sandpapers of 40 μm, 12 μm, and 3 μm and then the substrates were immersed in 1 N HCl for 1 minute. The treated HAp substrates were washed with ion-exchange water, dried, and put in a 24-well plate, to which 1 mL of each of the obtained compositions in Examples and Comparative Examples was added, followed by shaking for 5 minutes. The shaking was carried out using a shaker (Bio-Shake iQ (WakenBtech Co., Ltd)) under conditions of room temperature (25° C.) at 500 rpm. Subsequently, each of the compositions was sucked up, 1 mL of ion-exchange water was added, followed by shaking for 5 minutes. Then the water was sucked up to obtain treated substrates.

2) Collection of Stimulated Saliva

Healthy male in the twenties and thirties as subjects were asked to chew gum pellets included in Dentbuff Strip (OralCare Inc.) and spit out the saliva accumulated in the mouth into a falcon tube each time to thereby collect the saliva in the falcon tube. Note that as bacteria in the saliva vary person to person, the saliva collected from one healthy male was subjected to a dental plaque dispersion effect test on all Examples and Comparative Examples.

3) Formation of Model Dental Plaque

The saliva collected in the falcon tube was centrifuged at 3,000 rpm/rt (25° C.)/10 min. The separated supernatant saliva was added with sucrose in such a way as to be a 5 mass % solution, and then stirred using a mixer (voltex, manufactured by NIPPON Genetics Co, Ltd.) to prepare a dental plaque model test solution.

Subsequently, 1 mL each of the dental plaque model test solution prepared above was added to the HAp substrates treated in 1), and then these were stored in a plastic case with a $CO_2$ pack to achieve an anaerobic condition and culturing was carried out at 37° C. for 48 hours.

4) Evaluation on Biofilm Formation Inhibitory Effect

The saliva in the plate was sucked up using a vacuum pump and 1 mL of ion-exchange water was added, followed by shaking for 5 minutes. Subsequently, the water was sucked up using the pump and 750 μL of a 0.1 mass % crystal violet (CV) solution was added, followed by shaking for 15 minutes.

Further, the CV staining solution was sucked up using the pump, 1 mL of ion-exchange water was added, followed by shaking for 5 minutes. This was repeated twice. Subsequently, the water was sucked up using the pump, 500 μL of ethanol was added, followed by pipetting. Then the extract was diluted 10-fold with ion-exchange water to measure an absorbance at $OD_{595\ nm}$ using a microplate recorder (manufactured by Tecan Group Ltd., tunable wavelength absorbance microplate reader, Sunrise rainbow thermo).

Further, using an absorbance at $OD_{595\ nm}$ (initial value) obtained only by washing with ion-exchange water without using the above obtained compositions as a reference, a dental plaque formation rate (%) was calculated according to the formula below.

Note that the smaller an obtained dental plaque formation rate is, the higher a biofilm formation inhibitory effect is.

Dental plaque formation rate (%)={$OD_{595\ nm}$ of a substrate treated with the above described composition/$OD_{595\ nm}$ of the untreated substrate}× 100

«Foaming Evaluation Test»

Three panelists carried out sensory evaluation according to the following criteria on foaming when each of the obtained compositions was applied to the oral cavity.

A: Foamed very well with a very good feel upon use
B: Foamed well with a good feel upon use
C: Hardly foamed but no discomfort feels upon use
D: Poor foaming with a discomfort feel upon use «Evaluation Test on Low Temperature Storage Stability»

Each of the obtained compositions was filled in a glass bottle and stored at −5° C. for 3 days, then the content of liquid oral composition was visually observed from the outside of the glass bottle and evaluated according to the following criteria.

A: Completely transparent and homogeneous
B: Generally transparent and homogeneous
C: Rather turbid and semitransparent
D: Deposit was confirmed

TABLE 2

| | | Example 1 | Example 2 | Example 3 | Example 4 | Example 5 | Example 6 | Example 7 | Example 8 | Example 9 |
|---|---|---|---|---|---|---|---|---|---|---|
| Production Example of component (A) and component (B) | | I | I | I | I | I | I | I | II | III |
| Composition (mass %) | Total content of component (A) and component (B) | 0.03 | 0.03 | 0.03 | 0.03 | 0.03 | 0.03 | 0.01 | 0.03 | 0.03 |
| | Component (C) β-glycyrrhetinic acid | — | — | — | 0.03 | — | — | — | — | — |
| | Component (C) isopropyl methylphenol | 0.01 | 0.02 | 0.02 | — | — | 0.01 | 0.04 | 0.02 | 0.02 |
| | Component (C) triclosan | — | — | — | — | 0.02 | — | — | — | — |
| | Sodium lauryl sulfate | — | — | — | — | — | — | — | — | — |

TABLE 2-continued

|  |  |  |  |  |  |  |  |  |  |
|---|---|---|---|---|---|---|---|---|---|
| POE hydrogenated castor oil | — | — | — | — | — | — | — | — | — |
| Component (D) calcium chloride | 0.01 | 0.01 | — | 0.01 | 0.01 | 0.1 | 0.01 | 0.01 | 0.01 |
| Component (D) magnesium chloride | — | — | 0.01 | — | — | — | — | — | — |
| Ion-exchange water | Balance | Balance | Balance | Balance | Balance | Balance | Balance | Balance | Balance |
| Total | 100.0 | 100.0 | 100.0 | 100.0 | 100.0 | 100.0 | 100.0 | 100.0 | 100.0 |
| Content of component (A) in total content of component (A) and component (B) | 20.0 | 20.0 | 20.0 | 20.0 | 20.0 | 20.0 | 20.0 | 10.0 | 14.0 |
| Mass ratio of content of component (C) to total content or component (A) and component (B) ((C)/{(A) + (B)} | 0.3 | 0.7 | 0.7 | 1.0 | 0.7 | 0.3 | 4.0 | 0.7 | 0.7 |
| Amount of Component (C) (μmol/cm²) adsorbed on Hap substrate (μmol/cm²) | 0.08 | 0.12 | 0.09 | 0.16 | 0.11 | 0.10 | 0.09 | 0.06 | 0.09 |
| Plaque formation rate (%) | 18 | 12 | 21 | 41 | 28 | 20 | 38 | 49 | 33 |

|  | Example 10 | Example 11 | Example 12 | Example 13 | Example 14 | Example 15 | Comp. Ex. 1 | Comp. Ex. 2 |
|---|---|---|---|---|---|---|---|---|
| Production Example of component (A) and component (B) | III | I | I | I | I | I | — | — |
| Composition (mass %) Total content of component (A) and component (B) | 0.03 | 0.03 | 0.03 | 0.03 | 0.03 | 0.3 | — | — |
| Component (C) β-glycyrrhetinic acid | 0.03 | — | — | — | — | — | — | — |
| Component (C) isopropyl methylphenol | — | — | — | — | — | — | 0.02 | 0.02 |
| Component (C) triclosan | — | 0.05 | 0.1 | 0.02 | 0.02 | 0.02 | — | — |
| Sodium lauryl sulfate | — | — | — | — | — | — | 0.03 | — |
| POE hydrogenated castor oil | — | — | — | — | — | — | — | 0.1 |
| Component (D) calcium chloride | 0.01 | 0.01 | 0.01 | 0.001 | 0.2 | 0.01 | 0.01 | 0.01 |
| Component (D) magnesium chloride | — | — | — | — | — | — | — | — |
| Ion-exchange water | Balance | Balance | Balance | Balance | Balance | Balance | Balance | Balance |
| Total | 100.0 | 100.0 | 100.0 | 100.0 | 100.0 | 100.0 | 100.0 | 100.0 |
| Content of component (A) in total content of component (A) and component (B) | 140 | 20.0 | 20.0 | 20.0 | 20.0 | 20.0 | — | — |
| Mass ratio of content of component (C) to total content or component (A) and component (B) ((C)/{(A) + (B)} | 1.0 | 1.7 | 3.3 | 0.7 | 0.7 | 0.07 | — | — |
| Amount of Component (C) (μmol/cm²) adsorbed on Hap substrate (μmol/cm²) | 0.07 | 0.19 | 0.29 | 0.03 | 0.19 | 0.09 | ND | ND |
| Plaque formation rate (%) | 55 | 21 | 12 | 59 | 22 | 56 | 71 | 89 |

TABLE 3

|  | Example 5 | Example 15 | Example 16 | Comparative Example 3 | Comparative Example 4 |
|---|---|---|---|---|---|
| Production Example of component (A) and component (B) | I | I | I | — | — |
| Composition (mass %) Total content of component (A) and component (B) | 0.03 | 0.3 | 1.0 | — | — |
| Component (C) β-glycyrrhetinic acid | — | — | — | — | — |
| Component (C) isopropyl methylphenol | — | — | — | — | — |
| Component (C) triclosan | 0.02 | 0.02 | 0.02 | 0.02 | 0.02 |
| Sodium lauryl sulfate | — | — | — | 0.03 | 1 |
| Component (D) calcium chloride | 0.01 | 0.01 | 0.01 | 0.01 | 0.3 |
| Component (D) magnesium chloride | — | — | — | — | — |
| Ion-exchange water | Balance | Balance | Balance | Balance | Balance |
| Total | 100.0 | 100.0 | 100.0 | 100.0 | 100.0 |
| Content of component (A) in total content of component (A) and Component (B) | 20.0 | 20.0 | 20.0 | — | — |
| Mass ratio of content of component (C) o total content of component (A) and component (B) ((C)/{(A) + (B)} | 0.7 | 0.07 | 0.03 | — | — |
| Low temperature storage stability | B | B | A | D | D |

What is claimed is:

1. An oral composition comprising the following components (A), (B), (C), and (D):
   (A) an olefin sulfonic acid having 14 or more and 20 or less carbon atoms or a salt thereof,
   (B) a hydroxyalkanesulfonic acid having 14 or more and 20 or less carbon atoms or a salt thereof,
   (C) one or more oil soluble active components selected from the group consisting of isopropyl methylphenol, triclosan, thymol, and β-glycyrrhetinic acid, and
   (D) a water-soluble alkali metal salt,
   wherein the total content of the component (A) and the component (B) is 0.001 mass % or more and 2.5 mass% or less, and the content of the component (A) is 3 mass % or more and 50 mass % or less in the total content of the component (A) and the component (B).

2. The oral composition according to claim 1, wherein the mass ratio of the content of the component (C) to the total content of the component (A) and the component (B), ((C)/{(A)+(B)}), is 0.01 or more and 6 or less.

3. The oral composition according to claim 1, wherein the mass ratio of the content of the component (C) to the content of the component (D), ((C)/(D)), is 0.1 or more and 20 or less.

4. The oral composition according to claim 1, wherein the total content of an olefin sulfonic acid having a sulfonic acid group at position 2 of an olefin chain or a salt thereof in the component (A) and a hydroxyalkanesulfonic acid having a sulfonic acid group at position 2 of an alkane chain or a salt thereof in the component (B) is 5 mass % or more and 30 mass % or less in the total content of the component (A) and the component (B).

5. The oral composition according to claim 1, wherein the component (A) has 16 or more and 18 or less carbon atoms, and the component (B) has 16 or more and 18 or less carbon atoms.

6. The oral composition according to claim 1, wherein the component (D) is one or more selected from the group consisting of a calcium salt, a magnesium salt, and a strontium salt.

7. The oral composition according to claim 1, wherein the pH at 25° C. of the composition is 6 or more and 11 or less.

8. The oral composition according to claim 1, wherein a content of the component (D) in terms of salt is 0.001 mass % or more and 1 mass % or less.

9. The oral composition according to claim 1, wherein the total content of an olefin sulfonic acid having 18 carbon atoms or a salt thereof and a hydroxyalkanesulfonic acid having 18 carbon atoms or a salt thereof is 50 mass % or more and 100 mass % or less in the total content of the component (A) and the component (B).

10. A method for inhibiting formation of plaque comprising: applying an oral composition to the oral cavity, the composition comprising the following components (A), (B), (C), and (D):
    (A) an olefin sulfonic acid having 14 or more and 20 or less carbon atoms or a salt thereof,
    (B) a hydroxyalkanesulfonic acid having 14 or more and 20 or less carbon atoms or a salt thereof,
    (C) one or more oil soluble active components selected from the group consisting of isopropyl methylphenol, triclosan, thymol, and β-glycyrrhetinic acid, and
    (D) a water-soluble alkali metal salt,
    wherein the total content of the component (A) and the component (B) is 0.001 mass % or more and 2.5 mass % or less, and the content of the component (A) is 3 mass % or more and 50 mass % or less in the total content of the component (A) and the component (B).

11. The method according to claim 10, wherein the mass ratio of the content of the component (C) to the total content of the component (A) and the component (B), ((C)/{(A)+(B)}), is 0.01 or more and 6 or less.

12. The method according to claim 10, wherein the mass ratio of the content of the component (C) to the content of the component (D), ((C)/(D)), is 0.1 or more and 20 or less.

13. The method according to claim 10, wherein the total content of an olefin sulfonic acid having a sulfonic acid group at position 2 of an olefin chain or a salt thereof in the component (A) and a hydroxyalkanesulfonic acid having a sulfonic acid group at position 2 of an alkane chain or a salt thereof in the component (B) is 5 mass % or more and 30 mass % or less in the total content of the component (A) and the component (B).

14. The method according to claim 10, wherein the component (A) has 16 or more and 18 or less carbon atoms, and the component (B) has 16 or more and 18 or less carbon atoms.

15. The method according to claim 10, wherein the component (D) is one or more selected from the group consisting of a calcium salt, a magnesium salt, and a strontium salt.

16. The method according to claim 10, wherein the pH at 25° C. of the composition is 6 or more and 11 or less.

17. The method according to claim 10, wherein a content of the component (D) in terms of salt is 0.001 mass % or more and 1 mass % or less.

18. The method according to claim 10, wherein the total content of an olefin sulfonic acid having 18 carbon atoms or a salt thereof and a hydroxyalkanesulfonic acid having 18 carbon atoms or a salt thereof is 50 mass % or more and 100 mass % or less in the total content of the component (A) and the component (B).

* * * * *